United States Patent
Kasture et al.

(10) Patent No.: US 6,810,728 B1
(45) Date of Patent: Nov. 2, 2004

(54) KIT-BASED WIRE EVALUATION

(75) Inventors: Dnyanesh G. Kasture, Centreville, VA (US); Armin M. Bruning, Oak Hill, VA (US); Noel H. Turner, Springfield, VA (US); William G. Linzey, Reston, VA (US)

(73) Assignee: Lectromechanical Design Company, Dulles, VA (US)

(*) Notice: Subject to any disclaimer, the term of this patent is extended or adjusted under 35 U.S.C. 154(b) by 0 days.

(21) Appl. No.: 10/106,527

(22) Filed: Mar. 27, 2002

Related U.S. Application Data

(60) Provisional application No. 60/279,107, filed on Mar. 28, 2001.

(51) Int. Cl.[7] .............................................. G01B 21/08
(52) U.S. Cl. .................. 73/150 R; 73/150 R; 73/866; 73/864.41; 73/160; 73/865.6; 422/61; 382/145; 382/146; 382/148
(58) Field of Search ............................... 73/150 R, 866, 73/864.41, 160, 856.6, 865.6; 422/61; 382/145, 146, 147

(56) References Cited

U.S. PATENT DOCUMENTS

| | | | | |
|---|---|---|---|---|
| 464,125 A | * | 12/1891 | Varley | ........................ 324/544 |
| 4,517,252 A | * | 5/1985 | Hugh | ........................ 428/553 |
| 5,485,398 A | * | 1/1996 | Yamazaki et al. | .......... 356/397 |
| 5,676,580 A | * | 10/1997 | Farrar | ........................ 446/34 |

OTHER PUBLICATIONS

Maxim Intergrated Products, "1–Wire MicroLAN Evaluation kit" Nov. 22, 1999.*

* cited by examiner

*Primary Examiner*—Hezron Williams
*Assistant Examiner*—André K. Jackson
(74) *Attorney, Agent, or Firm*—Sughrue Mion, PLLC

(57) ABSTRACT

To provide an evaluation of the remaining life (level of insulation degradation) of wire in an installation, a kit-based approach avoids the need for technical personnel to visit a customer location. The kit includes equipment and instructions for selecting specimens for removal, capturing pre-removal information, removing the specimens, and sending the specimens for evaluation. A round form padded with protective material simplifies packing of the specimens while avoiding customer damage to the specimens. Accelerated aging testing and comparison between results for specimens from zones particularly susceptible to aging and one or more reference specimens permits an evaluation of remaining wire life.

3 Claims, 3 Drawing Sheets

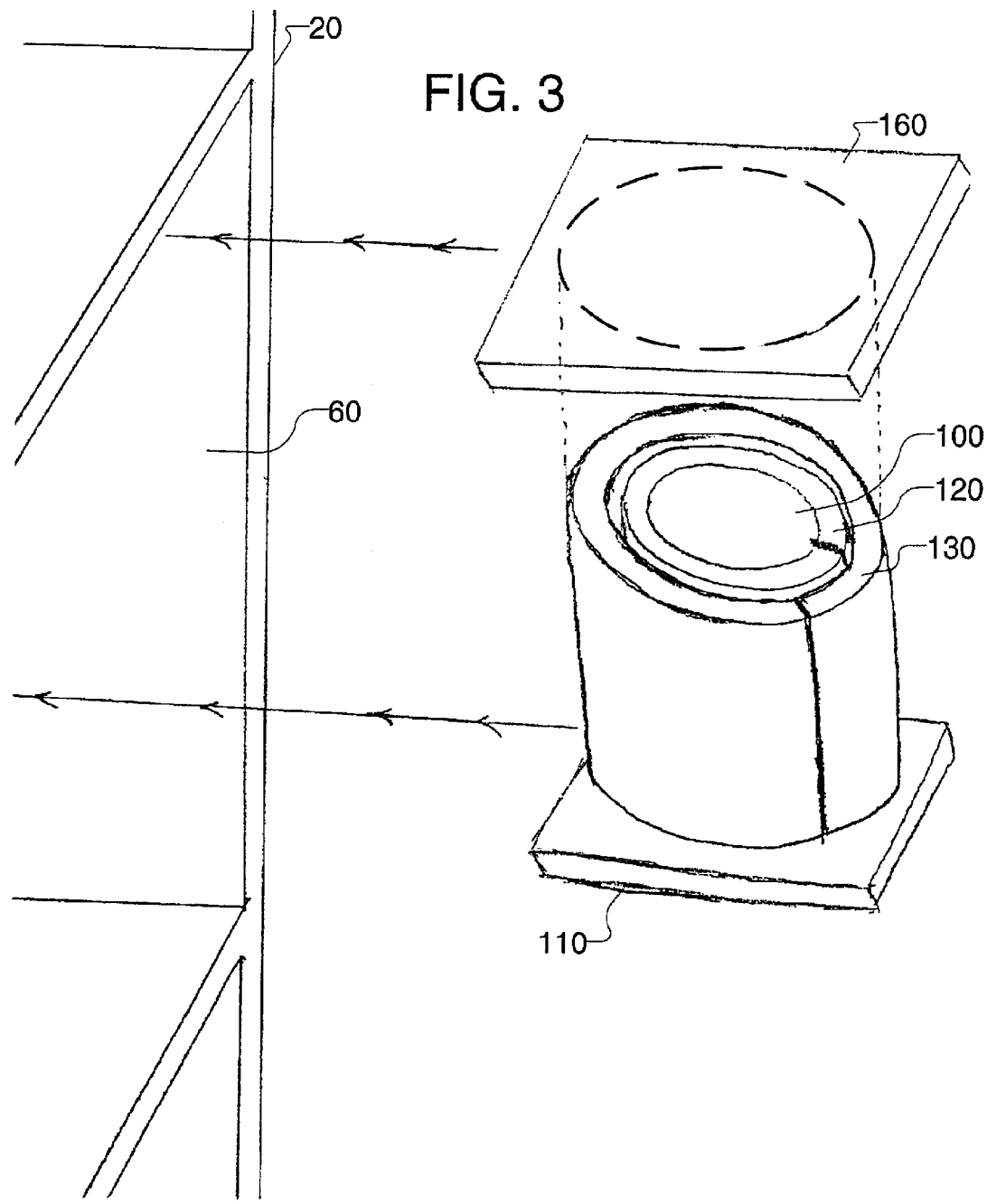

KIT-BASED WIRE EVALUATION

CROSS-REFERENCE TO RELATED APPLICATIONS

This application claims the benefit of U.S. Provisional Application No. 60/279,107, filed Mar. 28, 2001, confirmation No. 9502, which is incorporated by reference, herein, in its entirety.

FIELD OF THE INVENTION

This invention relates to the evaluation of wires for insulation degradation, sometimes referred to as "aging".

BACKGROUND OF THE INVENTION

Many complex systems involve substantial amounts of wiring and wiring harnesses. Examples of such systems include aircraft, ships, power plants, factories, vehicles, spacecraft, and missiles. Although the aging of wire was not recognized until recently, it has now been established that aging is one reason for the failure of wire.

To be more specific, the insulation surrounding the conductor may age, resulting in cracks, some of which cannot be detected by a visual inspection. Such cracks can permit such phenomena as arcing, with potentially disastrous results in systems such as aircraft in-flight.

Complex systems such as those mentioned above therefore require an evaluation of the wire to be performed even when the wire appears to be sound. Unfortunately, the wiring in such systems tends to be very long, run through bulkheads and other features which make its removal difficult or impossible, or be strapped down with connectors, retainers, and sleeves. In other words, the wire is in an "installation". When wire is in such an installation, it is typically impractical to effect the complete removal and evaluation of all the wire.

One approach to evaluating such systems' wiring is to evaluate some of the wiring in-situ. Such an evaluation may be performed, for example, according to the method described in U.S. Pat. No. 6,225,811, which issued on May 1, 2001 to Dr. Armin M. Bruning et al, and which is assigned in common with the present application to LECTROMECHANICAL DESIGN COMPANY of Sterling, Va.

For an evaluation of wiring at the installation according to any approach, however, highly skilled personnel are required for performing such an evaluation. Planning meetings are required. Much coordination may be necessary between the entity owning the system (often a government agency) and the entity performing the evaluation (often a contractor). Such meetings, preparation, coordination, and execution can be expensive and time-consuming. Moreover, given the great shortage of such highly skilled personnel in the industry, there is a practical limit to the number of systems that can be evaluated in the light of the fact that the personnel must travel to the system.

The same drawbacks exist in situations in which parts of the wire are removed from the installation and later tested by these highly skilled personnel. The personnel have to travel to the site, choose wire specimens for removal, oversee the removal, prepare the wire specimens for transport, and then test and provide results to the entity owning the system.

What is needed is a new approach to the evaluation of wiring in complex systems that avoids the deficiencies of present approaches.

SUMMARY OF THE INVENTION

According to one aspect of the invention, there is provided a kit-based approach to the evaluation of wiring. In this approach, the evaluation personnel do not need to travel to the system. Instead, a kit is sent from the evaluation personnel to the entity controlling the system ("customer" for the remainder of the discussion). The kit includes the necessary instructions and equipment for the customer to effect a safe and trouble-free removal of appropriate wire specimens from the system, the necessary instructions and equipment for the customer to preserve pre-removal environmental information, the necessary instructions to make intelligent selections for the selection of wire specimens, and the appropriate protective packing environment to ensure the specimens are not damaged during shipment.

Because the customers select the wires for removal, remove the wires, and send them to the evaluation personnel, it is no longer necessary for the evaluation personnel to travel to the system to perform the evaluation. This overcomes the above identified problems with the known approaches.

The manner in which the foregoing object is achieved, as well as other objects, will become clear from reading the description below which teaches the invention by way of various specific exemplary embodiments explained in detail, and further by way of various specific illustrations in the enclosed drawing figures.

BRIEF DESCRIPTION OF THE DRAWINGS

The drawing figures depict, in highly simplified schematic form, embodiments reflecting the principles of the invention. Many items and details that will be readily understood by one familiar with this field have been omitted so as to avoid obscuring the invention. In the drawings:

FIG. 3 shows how the round form and plate can be accommodated in a kit as shown in the embodiment of FIG. 1.

DETAILED DESCRIPTION

The invention will now be taught using various exemplary embodiments. Although the embodiments are described in detail, it will be appreciated that the invention is not limited to just these embodiments, but has a scope that is significantly broader. The appended claims should be consulted to determine the true scope of the invention.

The presently preferred embodiment of the invention relates to testing wire from aircraft. It will be appreciated, however, that the invention is not limited to the aircraft industry, but finds applicability in any variety of industries such as those already mentioned in a previous section, above.

Description of Kit

The kit sent to the customer can take any number of forms. There is no need for the kit to consist of only one container, and it is possible for the kit to comprise several containers. This section describes the presently preferred embodiment.

Figure 1:
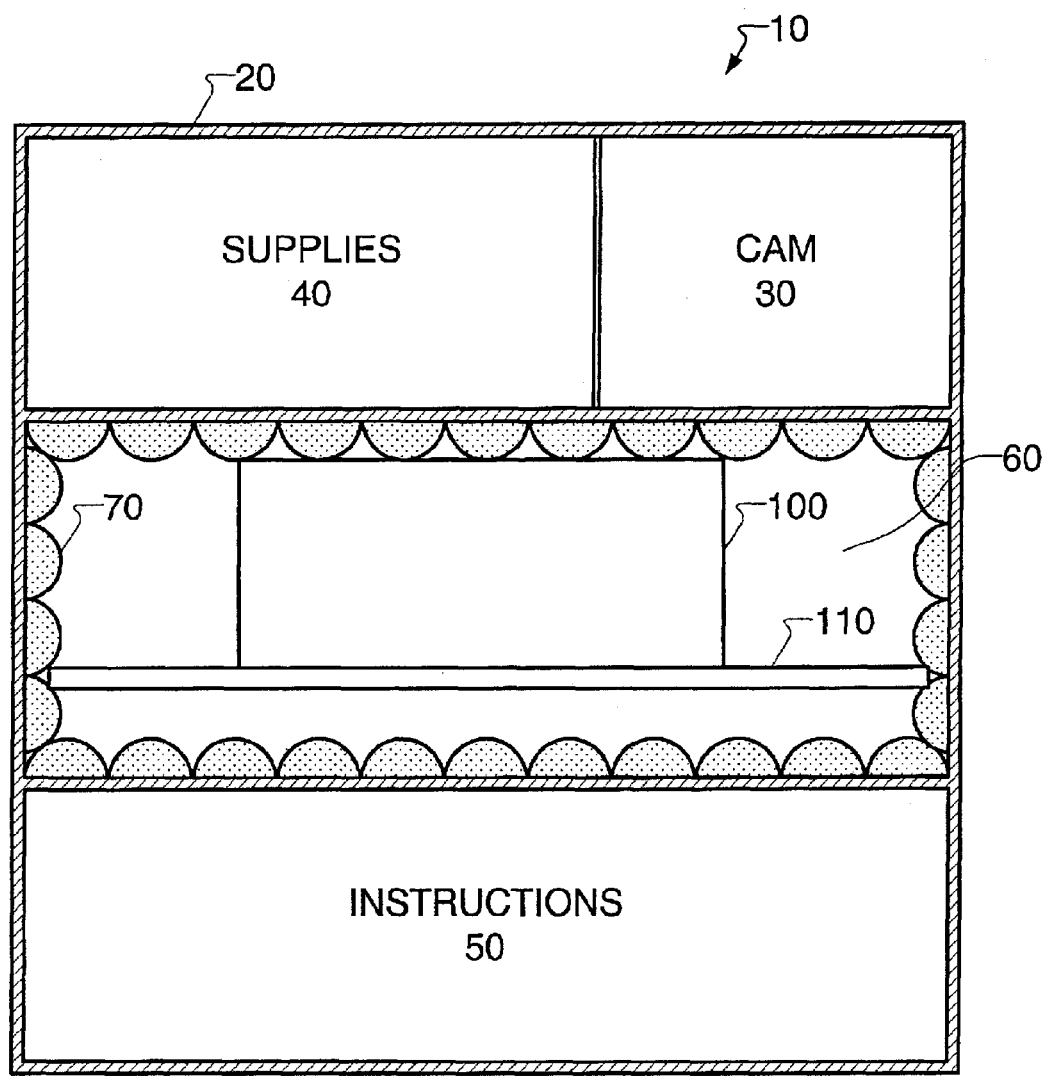
FIG. 1 is a highly simplified schematic view of a kit according to one embodiment.

The presently preferred embodiment is shown in FIG. 1. The kit indicated generally by reference numeral 10 includes supplies 40 such as a reference grid, a ball point pen, a magic marker, 3×5 cards, reference tape, a return address label, packaging tape, cushioning material; a camera CAM 30; instructions 50 including an instructional videotape and written instructions; a packing box 20; a central compartment 60 in the packing box, with cushioning material 70 on the inside of the central compartment; and a round form 100 on a plate 110.

The reference grid, in this embodiment, is a stiff board having printed on it a grid with lines spaced at a predetermined distance such a one inch. Placing the reference grid in a photograph of the wire specimen prior to removal of the specimen helps give the technical personnel an improved idea of the situs from which the specimen was removed.

The preferred reference tape is catalog number 11-880G ½ inch blue tape available from FISHER supplies. This tape is preferred because it is sticky enough to stick to the wire, is easy to write on with a ball point pen, resists smudging of the writing, and shows up distinctively in photographs.

The round form is provided with a diameter determined based on an expected property of the wire specimens that the customer will probably collect. The purpose of the round form is to provide a shape around which long wire may be wrapped without unduly stressing the specimen's insulation. The expected property that should be evaluated is the anticipated stiffness of the wire. Very thin wire, such as aromatic polyimide aircraft wire, should be wrapped around a round form of about 1 foot in diameter. This helps prevent the cracking of the insulation due to the wrapping. Thicker wire will require a larger diameter to the round form.

Figures 2A, 2B, 2C:
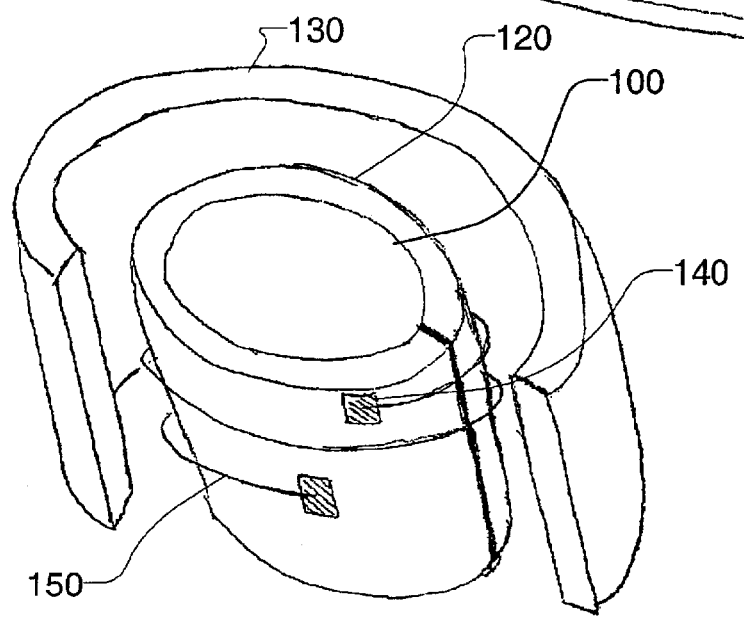
FIG. 2a shows a round form on a plate with square corners.
FIG. 2b shows a protective tread around the round form.
FIG. 2c shows a wire around the protective tread, and a round form cover.

Referring to FIGS. 2*a* and 2*b*, the round form 100 may be thought of as a being wheel-shaped, with a "tread" 120 around the wheel being made of a cushioning material, preferably styrofoam. Styrofoam is preferred because it will not harm the wire specimen, but is sufficiently resilient to give a surface about which the specimen may be firmly wrapped.

A round form cover 130 as shown in FIG. 2*c* may be provided to help protect the specimen 150 (wound around the round form) from contact with other objects. The cover may be made of a cushioning material, preferably styrofoam, bubble wrap, or the like.

The camera may be of any type, even a disposable camera.

The video tape may be any audiovisual format, and need not be a video tape. For example, a DVD or the like would be acceptable.

The cushioning material is provided for protecting wire specimens. Wire specimens having dimensions smaller than the packing box may be protected by being wrapped in the cushioning material without using the round form. Wire specimens having dimensions larger than the packing box may be protected by being wrapped around the round form, and then by being wrapped with the round form cover.

The packing box is preferably lined with cushioning material 70, at least in a part. That is to say, the packing box may include a subcompartment 60 adapted to the size of the round form 100, and the subcompartment may be the part of the packing box 20 lined with the cushioning material 70.

The packing box may have subcompartments or other adaptations to receive the video tape, the camera, the pen, the marker, the reference grid, or any other items sent to the customer or returned by the customer.

Description of Wire Removal Method

The customer receives in the kit instructions on performing the removal of the wire. The instructions help explain to the customer how to select suitable specimens, how to capture environmental information prior to removal, how to remove the wire, and how to pack the wire for return in the packing box.

Preliminary Considerations

Customers routinely replace wires when they are known to be damaged. Such known-bad wires are removed by the customer without any concern for preserving the bad wire. This makes sense, because the wire will be discarded.

Customers removing wires as specimens for evaluation can hardly be expected to intuitively treat such a wire removal operation any differently than the familiar removal of known-bad wires. Even so, it is essential, when removing wire specimens for aging evaluation, that the specimens suffer no additional "aging" due to the removal, or due to the packaging, or due to the shipping.

If a specimen to be evaluated is removed in the same manner as a known-bad wire is removed, it will almost necessarily suffer so much additional stress that the final test results will be altered.

Specimen Selection

The specimen selection method should include the selection of only wire original to the aircraft at the time of manufacture, retrofit, modification. It may be acceptable to use wire that is not original if it has been on the aircraft a long time, but such wire should be properly identified (see below). It is generally fruitless to attempt to obtain an overall idea of the aging of wire in an aircraft by testing wire recently replaced.

The specimen selection method may include a selection based on an approved gauge. For example, wires in aircraft are typically of the aromatic polyimide type. Such wires appear in a variety of gauges, such as 20, 22, 26. There are gauges lower than 20 (e.g., 16, 12, . . . ). AWG 26 wire, however, is unacceptable because of the great variability in its manufacture. Gauges 20 and 22 are greatly preferred to 26 for this reason when evaluating aromatic polyimide insulated wiring. Likewise, all the specimens taken preferably have an identical gauge.

The specimen selection method should include making selections of only specimens that are unshielded, untwisted, undamaged, unprotected, and/or free of splices. Although there are special ways to evaluate shielded wires, since the major components of aging are humidity and temperature, specimens that are shielded cannot normally provide helpful information as to the state of aging of the remainder of the unshielded wire in the aircraft. The same may be said for wires protected by sleeves or heat-shrink tubing. Spliced wire specimens include breaks in the insulation and cannot provide helpful information as to the state of aging of the remainder of the unspliced wire in the aircraft. Twisted wire is not very useful because customers tend to break or damage the insulation when untwisting the wire, and because twisted wire needs special handling in testing in order to generate useful results.

As the foregoing points show, the goal is not to obtain an idea of how good the condition of some of the wiring may be, but to provide an idea of how bad the condition of some of the wiring might be due to aging. To this end, the wire specimen should also visually appear undamaged. Visible damage is damage normally due to some acute cause, and not aging, and such damaged specimens are not useful.

The method of specimen selection should include selecting wires from zones particularly susceptible to aging. Examples of such zones are installations exposed to high temperature, to high humidity, and/or to a significant number of tight bends. Other such zones may be determined based on historical data such as high field trouble occurrences in a fleet's epidemiology database, or recurring complaints of unreliable equipment from electrical maintenance personnel.

The method of specimen selection should also include selecting some wire that is from a protected environment for use in comparison with the wire from zones particularly susceptible to aging.

The method of specimen selection, when performed for multiple aircraft, should be performed so as to select the exact same wires in the exact same locations across the multiple aircraft to get the best sample, however, deviations are acceptable. In other words, the selection should be uniform across plural identical or substantially similar systems.

Capture of Pre-Removal Environmental Information

One goal is to avoid the need for technical personnel to visit the site by having the customer select and provide the specimens. Information about the wire's disposition in-situ, prior to removal, is often very helpful in estimating wiring aging.

To this end, certain pre-removal environmental information is captured.

A method of capturing pre-removal environmental information should include imaging the situs of each specimen prior to removing the specimen This imaging may be performed with a camera, video, or the like. Of course, a thorough textual description could suffice, but the use of imaging saves significantly on time, and avoids variability in the accurateness of customer textual descriptions.

The imaging operation should include a step of including a reference grid in the image in the vicinity of the specimen to be removed. The reference grid may be held in position for the taking of the image by a person or by tape.

The imaging operation should include labeling of the specimen in a manner that records any or all of the following: description of the location of the wire; aircraft identifier (such as tail number); type/model/series numbers of the aircraft. It is preferable to use the 3×5 cards for this, and to tape the cards in the vicinity of the wire to be removed so that they appear in the image. This step may be thought of as making a descriptive record of the specimen.

The method of imaging should include a step of pre-removal visual identification. Pre-removal visual identification, in the presently preferred embodiment, simply involves putting a piece of colored tape at one end of the wire to be removed. The tape should be positioned at about half an inch or an inch from where the cut will be, preferably in a manner consistent with the in-situ environment. One example of a manner consistent with the in-situ environment is to always place the tape at an end closest to the next connecter. Other approaches can be taken, depending on the situation. For example, with a utility, the visual indicia could always be placed at the end closest to the customer.

When multiple similar samples are taken from various identical installations, such as samples across several aircraft, the samples taken should be the same in each aircraft, and should be marked the same.

After including the reference grid, making a descriptive record of the specimen, and performing preremoval visual identification, the imaging operation is performed. It is preferred that the imaging operation include a plurality of images taken from a variety of positions.

Specimen Removal

The specimen removal method should include loosening all cable clamps and ties. Normally, when a known-defective wire is removed, it is simply yanked out, pushed through, bent, strained, and treated harshly. Such treatment is definitely harmful to the wire, and will certainly skew the results of any evaluation.

Therefore, cable clamps and ties should be loosened or removed so that the wire can be removed without any such damage. Bending should be avoided. The visual indicia, such as colored tape, which was placed on the wire during the capture of pre-removal environmental information, should be removed so that it does not catch on clamps or ties.

After the actual removing of the specimen, the visual indicia should be reattached at the original location.

Manufacturers typically label the wires with specification numbers and numbers that indicate the manufacturer. Sometimes, the wires will have a circuit number identifier. This information which is borne on the outside of the wires may be thought of as integral identification information. This integral identification information should be recorded.

For each specimen, it is often beneficial to record contextual environmental information. Contextual environmental information, as used here, means information such as the pin or terminal number to which the wire connects; the reference designation of the terminations; the type of environment for the zone, including temperature, relative humidity, and bends; history relating to the zone from which the specimen was removed, such as modification time and location history for the particular installation, such as where the aircraft or other vehicle has been located during its deployed life.

Finally, for each specimen, removal information such as the dates the samples were removed, and personnel involved, should be recorded.

Packing of the Specimens

The packing of the specimens is preferably performed in different ways depending on the dimensions of the specimens. When the dimensions of the specimen, including its normal "memorized" shape, do not exceed the dimensions of the shipping box (i.e., fit in the appropriate compartment 60), then the specimen is simply wrapped with a protective material such as bubble wrap and enclosed with its tags (visual indicia and the descriptive record).

On the other hand, when the dimensions of the specimen exceed the dimensions of the shipping box, then the specimen is bent into a loop of no less than about 1 foot in diameter, for aromatic polyimide wiring found in aircraft. To facilitate this bending, and to avoid the necessity for the customer personnel to correctly gauge the diameter of a loop, the round form is provided.

To use the round form 100 (see FIGS. 2*a–c*), the customer tapes 140 one end of the wire 150 to the round form (or to the cushioning tread 120 if provided); this end now defines the standing end of the wire. The customer then wraps the free end of the wire around the round form. The round form has a diameter that is appropriate to the type of wire being evaluated. For wire such as aromatic polyimide wire from aircraft, the 1 foot diameter is appropriate for the round form. For other wires, the diameter of the round form needs to be determined based on what kind of wire the customer is expected to send back. In other words, the round form is provided with a diameter determined based on an expected property (in this case, stiffness of the insulation and size of the wire) of the wire specimens. For larger harnesses/wire samples, a larger dimension box is used.

Once the wire has been wrapped around the round form, the free end is also secured to the round form using tape 140.

The round form cover 130 is optionally placed over the wire 150 and the whole assembly is placed into the appropriate compartment 60 of the shipping box 20.

The round form may be provided in such a manner that it is already secured to a flat plate with square corners, as shown in drawing FIG. 3. The advantage of the flat plate is that it helps keep the wire from coming off the round form. The advantage of having square corners on the flat plate is that it helps keep the round form from moving around the shipping box if the size of the flat plate is adapted to the size of the compartment 60 of the shipping box 20. That is to say, the flat plate is provided with length and width dimensions that fit within the shipping box's compartment and restrict movement of the flat plate. Of course, it is preferred that the flat plate, when provided with square corners, includes edges that are smoothed out so that there are no sharp edges.

It is possible to have two such plates, one on either side of the round form (see FIG. 3). Although such an arrangement provides an advantage in retaining the wire around the round form, it makes it harder for the customer personnel to wrap the wire around the round form. Therefore, the preferred embodiment of the round form includes only one flat plate or a removable second flat plate that can be put on the round form after wrapping the: wire 150.

One other advantage of the round form is that it prevents the customer personnel from coiling a wire specimen into a loop, and then holding the wire in this position by putting tape around the coiled wire in such a manner that the tape passes through the center of the loop. This should be avoided because it can pinch the wires together, and cause damage to the insulation, thereby giving false test results.

The shipping box is then provided to the evaluation personnel.

Description of Wire Evaluation Method

Various methods of wire evaluation are known. Any wire evaluation method that provides a results in which the customer has interest is appropriate to use. Examples of such methods of wire evaluation that will be familiar to one experienced in this field include physical and mechanical tasks, chemical tests, environmental tests, and electrical tests.

Examples of physical and mechanical tests include detailed visual inspection, breach location inspection, photo microscopy, Cross-section evaluation, dimensional evaluation, indenter modulus testing, tensile strength testing, elongation testing, bend/wrap/mandrel testing, flex life testing, notch propagation testing, and cut through testing.

Examples of chemical tests include infrared spectroscopy, viscosity, visible spectroscopy, UV spectroscopy, differential scanning calorimetry, and oxidation induction time.

Examples of environmental testing include humidity resistance, forced hydrolysis, thermal index, thermal gravimetric analysis, and fluid immersion testing.

Examples of the electrical testing include insulation resistance, dielectric breakdown voltage, voltage withstand (wet dielectric), corona inception/extinction voltage, arc track resistance (wet/dry), and time/current to smoke.

One particularly preferred testing method is an accelerated aging test. An accelerated aging test is especially suitable for testing aromatic polyimide wiring. To perform an accelerated aging test, a two foot section of wire is used. Some insulation is removed from each end of the wire, and the ends are connected to a voltage source. The wire is stressed by being wrapped around a mandrel and immersed in high temperature conducting fluid (such as water at 95 degrees Celsius, for example). The wire is thus exposed to high humidity and high temperature at the same time. This provides a highly accelerated aging process. By putting a voltage on the conductor through the insulation to the conducting fluid, the presence of and the amount of leakage current through the insulation can be determined.

The point at which the wire under test in an accelerated aging test fails can be correlated against other test samples to provide an evaluation of the percentage to which the wire has aged. Using this, an estimate can be provided as to the remaining life of the wire.

It is preferred that the specimen being tested for aging or any other quality is compared with wire from the same aircraft. Wire from the same aircraft, in good shape, is substantially representative of the age of the aircraft. Its performance on the accelerated aging test (or any of the other above-mentioned tests) provides an appropriate benchmark against which to measure the other specimens. Naturally, the other specimens should be taken from areas of concern. Wire from the same aircraft in a benign area is generally in good shape, and is very close to the original quality of all similar wire on the aircraft.

The results of the testing may also be compared with results of testing specimens from the rest of the fleet and with other similar results logged in a wire aging database (discussed below). This kind of information can provide important insights for the entity controlling the fleet.

When the customer fails to provide wire from the same aircraft, in good shape, it is possible to use wire from a similar aircraft of similar age, if available. It is also possible to compare the specimens provided against brand new wire, although this is not as desirable.

Finally, it is possible to compare the specimens provided against substantially identical wire which varies from the construction and material of the specimen in only insubstantial ways.

The comparisons just mentioned do not always have to be performed anew. In one preferred embodiment of the invention, a database is consulted. The database may be thought of as a wire aging database or a wire testing database. The wire aging database includes information from tests previously made. The information includes test results for various types of wire, various specifications, various manufacturers, and various tests. The database can also include a correspondence table that indicates correspondence between various military and civilian specifications for wire.

For the sake of generality, therefore, it will be understood that the term "reference specimen" can mean a specimen of the same wire taken from the same aircraft, a new wire, a wire from a similar aircraft, or data from a database. Using a specimen of the same wire taken from the same aircraft as the reference specimen is the most preferred, as mentioned above.

Conclusion

The contributions of the invention described by way of the foregoing exemplary embodiments are very significant. One significance is that there is now provided a kit-based wire evaluation method that avoids the need for highly skilled personnel to perform certain functions on site by virtue of providing a kit, a wire removal method, and a wire evaluation method. The wire removal method includes specimen selection, capture of pre-removal environmental information, actual removal of specimens, and packing of the specimens.

Cost of the testing is thus decreased. Because the cost is significantly decreased, the invention provides a quick, inexpensive way to do follow up testing. A periodic test performed can help detect whether there is a change in rate in the aging of wire.

Another important contribution is the inexpensive method of providing results for not just a single aircraft or other entity, but results that are obtained across multiple aircraft and give comparative information across the fleet.

Many variations to the above-identified embodiments are possible without departing from the scope and spirit of the invention. Possible variations have been presented throughout the foregoing discussion. Moreover, it will be appreciated that wherever the term "aircraft" is used, the teaching at that point should be understood to apply to any given wire installation in a location in which the wire must be removed for the conduct of the testing.

Combinations and sub-combinations of the various embodiments described above will occur to those familiar with this field, without departing from the scope and spirit of the invention.

What is claimed is:

1. A kit-based wire evaluation method, comprising:

providing a kit to a customer; then selecting specimens for removal from an installation, capturing pre-removal environmental information, and removing the specimens from the installation; then providing wire specimens and the kit to a test facility; and then performing an evaluation of the wire specimens at the test facility; wherein capturing pre-removal environmental information includes imaging the specimen prior to removal from the installation; wherein the imaging is performed by the customer with a camera included in the kit.

2. A kit-based wire evaluation method, comprising:

providing a kit to a customer; then selecting specimens for removal from an installation, capturing pre-removal environmental information, and removing the specimens from the installation; then providing wire specimens and the kit to a test facility; and then performing an evaluation of the wire specimens at the test facility; wherein performing the evaluation of the wire specimens at the test facility includes an accelerated aging test; then making a comparison between the point at which the wire specimen under test in the accelerated aging test fails with a point at which a reference wire specimen fails in the accelerated aging test.

3. The wire evaluation method as set forth in claim 2, further comprising:

providing an evaluation of the remaining life of the wire in the installation based on the comparison.

* * * * *